United States Patent [19]

Lai et al.

[11] 4,415,684

[45] Nov. 15, 1983

[54] UV-LIGHT STABILIZED COMPOSITIONS CONTAINING SUBSTITUTED 1,5-DIAZACYCLOALKANES

[75] Inventors: John T. Lai, Broadview Heights; Pyong N. Son, Akron, both of Ohio

[73] Assignee: The B. F. Goodrich Company, Akron, Ohio

[21] Appl. No.: 355,167

[22] Filed: Mar. 5, 1982

Related U.S. Application Data

[63] Continuation-in-part of Ser. No. 122,936, Feb. 20, 1980, abandoned, which is a continuation-in-part of Ser. No. 835,069, Sep. 21, 1977, Pat. No. 4,207,228.

[51] Int. Cl.³ .............. C07D 243/12; C07D 405/06; C07D 405/10; C08K 5/34
[52] U.S. Cl. .............. 524/92; 260/239 BC; 260/239 BD
[58] Field of Search .............. 260/239 BC, 239 BD, 260/45.8 N; 524/92

[56] References Cited

U.S. PATENT DOCUMENTS

| | | | |
|---|---|---|---|
| 2,899,359 | 8/1959 | Fancher et al. | 260/239 BD |
| 3,557,086 | 1/1971 | Cantore | 260/239 BC |
| 4,007,157 | 2/1977 | Ramey et al. | 260/45.8 H |
| 4,207,228 | 6/1980 | Lai et al. | 260/239 BC X |

*Primary Examiner*—Mary C. Lee
*Assistant Examiner*—D. B. Springer
*Attorney, Agent, or Firm*—Albert D. Lobo; Nestor W. Shust; Alan A. Csontos

[57] ABSTRACT

Novel compositions which are highly stable and resistant to degradation by ultraviolet (UV) light are prepared by dispersing polysubstituted 1,5-diazacycloalkanes in the material subject to degradation, particularly in polyolefins. The cyclic compounds of this invention have (a) a fixed three-carbon bridge between the $N^1$ and $N^5$ atoms of the diaza ring, the remaining portion of the ring having a variable length bridge of two or more carbon atoms, (b) an N-adjacent carbon atom of the diaza ring is polysubstituted, that is, has two substituents which may be cyclizable. Monocyclic 1,5-diazacycloalkanes are prepared by reducing the corresponding 2-keto-1,5-diazacycloalkane with metal hydride; bicyclic 1,5-diazacycloalkanes, particularly fused ring bicyclic compounds such as substituted 1,5-decahydrobenzodiazepines are prepared by reaction of a diaminocycloalkane with an unsaturated ketone or acid and reducing with metal hydride.

8 Claims, No Drawings

UV-LIGHT STABILIZED COMPOSITIONS CONTAINING SUBSTITUTED 1,5-DIAZACYCLOALKANES

CROSS-REFERENCE TO RELATED APPLICATIONS

This application is a continuation-in-part application of copending application Ser. No. 122,936 filed Feb. 20, 1980 now abandoned which is in turn a continuation-in-part of Ser. No. 835,069 filed Sept. 21, 1977, now issued as U.S. Pat. No. 4,207,228.

BACKGROUND OF THE INVENTION

Any material, whether natural or synthetic, must exhibit satisfactory resistance to degradation under conditions of use, if products made from the materials are to find a lasting market. A lack of satisfactory resistance to degradation usually manifests itself as a partial or total loss of structural integrity, a darkening or discoloration of the product, a loss of flexibility or resilience, or a combination of the above phenomena. These phenomena are promoted or catalyzed by air (oxygen), heat and light, particularly ultraviolet light.

To protect materials, ingredients which can be collectively called stabilizers are admixed with the materials to prevent or inhibit degradation. These stabilizers work in diverse and complex ways, such that a compound which stabilizes against heat and oxygen degradation in a material may not stabilize against light degradation in the same material, or vice versa. Furthermore, a compound which acts as a stabilizer against oxygen degradation in one type of material may be relatively inactive in another type of material. Thus compounds which are stabilizers are further classed as antioxidants, antiozonants, heat stabilizers and ultraviolet (UV) light stabilizers, depending upon what type of activity and stabilization they demonstrate. In many cases, to obtain optimum protection, a mixture of compounds, each specifically selected to afford maximum protection against a certain type of degradation, is often used. In some instances stabilizers are deliberately chosen to counter the adverse effects of a plasticizer which, though highly effective as a plasticizer, tends to accelerate UV degradation. In other words, the plasticized material is more susceptible to degradation than if no plasticizer was added. As a general empirical rule, it is found that plasticizers are marginally effective as stabilizers, and stabilizers are marginally effective as plasticizers, it being more likely that a compound with desirable stabilizer properties has undesirable plasticizer properties, and vice versa.

The present invention is directed to (a) novel UV light stabilizers classed as hindered amines more specifically classed as hindered cyclic diazaalkanes, and (b) novel compositions in which the cyclic diazacycloalkanes are incorporated. The basic structure of these novel compounds is a polysubstituted 1,5-diazacycloalkane having (a) a fixed three-carbon bridge between the two N atoms (the $N^1$ and $N^5$ atoms) of the diaza ring, the remaining portion of the ring having a variable length bridge of two or more carbon atoms, and (b) at least the $N^5$-adjacent carbon atom of the fixed three-carbon bridge has two substituents (hence "polysubstituted"), which may be cyclizable, that is, form a cyclic substituent. These compounds which may be monocyclic, or with cyclizable substituents, may be bicyclic or tricyclic, are particularly useful as UV light stabilizers in substantially colorless organic compounds, and particularly in polymeric substrates. They may also form dimers and bis-compounds. The diaza ring of the basic structure may have from 6 to 9 ring members, more preferably from 6 to 8 ring members, and most preferably from 6 to 7 ring members.

It is known that 2-keto-4,4,6,6-tetramethyl-1,5-diazacycloheptane may be prepared by a Schmidt's rearrangement of a six-membered ring with sodium azide (see German Pat. No. 2,428,877) but there is no known manner of similarly arriving at an eight membered, 1,5-diaza ring with an $N^1$-adjacent carbonyl. Moreover, though the foregoing 2-keto-diazacycloheptane, identified as 2,2,7,7-tetramethyl-5-oxo-1,4-diazacycloheptan in the reference, can be synthesized as described, other polysubstituted compounds named cannot be so synthesized. More specifically the 2-keto-1,5-diazapolycycloalkanes named therein cannot be synthesized as described. The foregoing lactams which may be made as described in this German patent, and many other lactams which may be made as described in U.S. Pat. Ser. No. 835,069, may be reduced, for example, with lithium aluminum hydride, to form the 1,5-diazacycloalkanes which are found, like the lactams, to be excellent UV light stabilizers.

It is known that 1,5-benzodiazepin-2-spirocycloalkanes may be made in a one-step condensation from o-phenylenediamine and cyclic ketones such as cyclohexanone in cold ethanol in the presence of boron trifluoride-ether complex. ("Synthesis of Hetrocyclic Compounds. Part XXIX. Substituted 2,3-dihydro-1H-1,5-benzodiazepines" by Herbert, John A. A. and Suschitzky, Hans, J. C. S. Perkin I, 1974, 2657.) However, 1,2-diaminocyclohexane does not react under similar conditions. The lactams of this reference may also be reduced with a metal hydride to yield the 1,5-diazacycloalkanes used in the composition of this invention.

Further, it is known that α,β-unsaturated ketones may be added slowly to a methanol solution of an aliphatic 1,2-diamine at about 30° C., and the mixture hydrogenated over an Adams catalyst to give 7-alkyl-1,5-diazacycloheptanes also identified as 2-alkyl-1,4-diazacycloheptanes (Bonvincini A. and Cantatore G., Chem. Ind. 54,980 (1972); New Methods in Synthetic Organic Chemistry Selected from the Current Chemical Literature, August 1974). There is no disclosure which might suggest the use of the substituted alkanes as UV light stabilizers in organic polymers.

It is also known that cyclo condensation of β,β-dimethylacrylic acid with o-phenylenediamine and its derivatives yields 2-keto-1,5-benzodiazepines (Khakimova, N. K. et al, Inst.Khim.Rast.Veshechestv, Tashkent, USSR: USB.Khim.Zh.1975, 19(2), P 53–55). The $N^5$-adjacent carbon of the fixed three-carbon ring is disubstituted, and the benzene ring may have a hydrogen, chlorine or methyl substituent. The reference compounds have no utility as UV light stabilizers. It has now been found that, under strenuous hydrogenating conditions of above about 200° C. and 2000 psi, the 2-keto-1,5-benzodiazepines of the Russian reference may be hydrogenated in alcohol to the 2-keto-decahydro-benzodiazepine without rupturing the ring structure, though we are aware of no teaching that would indicate a seven-membered, 1,5-diaza ring could withstand such strenuous conditions, or that such hydrogenation could be accomplished. Though the lactams are excellent stabilizers, it has been found that the alkanes, produced by reducing the lactams, are also excellent UV stabilizers.

In fact, known quinioline derivatives such as 1,2,3,4-tetrahydro-3,3,6 (or 7)-trimethylquinoline is not hydrogenated under similar conditions, namely 200° C. and 2000 psi in the presence of Raney's nickel, but decomposes.

Except for the 2-keto-1,5-diazacycloheptane compounds disclosed in the aforementioned German reference there is no teaching to suggest that polysubstituted 1,5-diazacycloalkanes and polycyclic polysubstituted 2-keto-1,5-diazacycloalkanes would be effective UV-light stabilizers.

SUMMARY OF THE INVENTION

UV-light-stable compositions have been discovered in which an organic compound particularly a polymeric substrate such as a polyhydrocarbon, polyester, polyester resin, polyamide, vinyl polymer, cellulose ether or cellulose ester, has uniformly dispersed therein, an effective amount of a polysubstituted 1,5-diazacycloalkane UV-light absorbing compound sufficient to make the organic compound UV light stable.

More specifically, novel UV-light-stable compositions have been discovered in which the stabilizers are polysubstituted 1,5-diazacycloalkanes having (a) a fixed three-carbon bridge between the N atoms of the diaza ring, the remaining portion of the ring having a bridge of variable length comprising from about two to about three carbon atoms, and (b) the $N^5$-adjacent carbon atom of the fixed three-carbon bridge has two substituents which may be cyclizable. When the variable length bridge contains only two carbon atoms, the diazacycloalkane compound may also be regarde as a 1,4-diazacycloalkane.

Though desirable stabilization of an organic compound may be obtained with two substituents on the $N^5$-adjacent C atom of the fixed three-carbon bridge of a diazacycloalkane, it has been discovered that additional substituents, including at least one particularly on the $N^5$-adjacent C atom of the variable length bridge, provides superior UV-light-stability.

It has further been found that, in addition to UV-light compositions which include aforementioned polysubstituted 1,5-diazamonocycloalkanes, excellent UV light stability may also be obtained with polysubstituted 1,5-diazapolycycloalkanes, all of which are preferably used in the range from about 0.1–1.0 part stabilizer per 100 parts organic compound or polymeric substrate to be stabilized.

It is therefore a specific object of this invention also to provide a UV-light-stable composition in which is uniformly dispersed a 1,5-diazapolycycloalkane, having two substituents which may be cyclizable, on the $N^5$-adjacent C atom in the fixed bridge; and preferably having a total of at least three substituents on the symmetrical $N^5$-adjacent C atoms, some of which substituents together with the C atoms to which they are bound, may be cyclizable.

More specifically, uv-light degradable normally solid polymers are stabilized against such degradation by incorporating therein a small but effective amount of a polycyclo-1,5-diazacycloalkane in which there may be a cyclic (spiro) substituent on the $N^5$-adjacent C atom of the diaza ring, or this C atom may be di-substituted with acyclic substituents, provided the basic structure of the stabilizer is bicyclic, that is, having a ring fused to the diaza ring.

It has also been discovered that diaminocycloalkanes may be reacted with $\beta,\beta$-dialkyl-substituted $\alpha,\beta$-unsaturated acids to yield a carbonylcontaining diaza ring such as a bicyclo-1,5-diazaalkan-2-one with a disubstituted $N^5$-adjacent C atom in the fixed three-carbon bridge of the diaza ring. The bicylo-1,5-diazaalkan-2-one with a disubstituted $N^5$-adjacent C atom may subsequently be reduced with a hydride such as lithium aluminum hydride, to yield a bicyclo-1,5-diazaalkane; or, the diaminocyclohexane may be reacted with an unsaturated ketone (monoketone) to yield a diaza ring containing a double bond which may subsequently be reduced with $LiAlH_4$. In an analogous manner, other di-substituted polycyclo-1,5-diazaalkan-2-ones and unsaturated diaza rings may be reduced.

Alternatively, orthophenylenediamine may be substituted for the diaminocyclohexane to form a bicyclo-1,5-diazaalkane-2-one in which the fused ring is phenyl. Upon hydrogenation over an Adam's catalyst or Raney's nickel, the phenyl ring is hydrogenated, and if the carbonyl on the diaza ring is not, subsequent reduction with $LiAlH_4$ yields the diazacycloalkane.

It is therefore a general object of this invention to provide novel UV stabilized compositions containing a polysubstituted bicyclo 1,5-diazacycloalkane in which the $N^5$-adjacent C atom of the fixed bridge has two substituents which may be cyclizable, particularly substituted benzodiazepines and decahydrobenzodiazepines, in which compositions a minor amount, generally less than 1 percent by weight, of the polysubstituted bicyclo 1,5-diazacycloalkane is present.

DETAILED DESCRIPTION OF PREFERRED EMBODIMENTS

Polysubstituted (hereinafter referred to as "substituted" for brevity) 1,5-diazacycloalkanes, in which at least the $N^5$-adjacent C atom of the fixed three-carbon bridge has two substituents which may be cyclizable, when incorporated into UV-light-degradable organic materials, exhibit a surprisingly powerful stabilizing effect. The stabilizers are used in the range from about 0.01 to about 1.0 percent, per 100 parts of organic compound subject to UV light. Compositions which include these stabilizers are conveniently and economically prepared. The UV stabilizing effect of these compounds, substantially disappears when each carbon of the diaza ring is unsubstituted, and the stabilizing effect is too slight to be practical even when each symmetrical $N^5$-adjacent C atom is monosubstituted. It is therefore essential for good stability, that the $N^5$-adjacent C atom of the fixed three-carbon bridge be disubstituted, or have a cyclic substituent, irrespective of the number of members in the diaza ring. It is preferred, for superior UV stabilizing performance, that some substituents on the diaza ring be cyclizable so as to provide a diazapolycycloalkane, such as a diazabicycloalkane or diazatricycloalkane. It is more preferred that the stabilizer compounds be bicycloalkanes having seven or eight membered 1,5-diaza rings, and that the $N^5$-adjacent carbon of the fixed three-carbon bridge be disubstituted with acyclic substituents. The variable length bridge has two or more C atoms and may have substituents on one or more of the C atoms of the variable length bridge, and these substituents may be cyclizable.

Compositions of this invention contain UV light stabilizers selected from the group consisting of 1,5-diazacycloalkanes having the structural formula

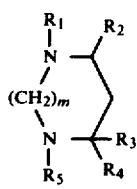

wherein, m represents an integer in the range from 2 to 7, being the number of methylene groups forming a bridge of variable length, and some of which groups (a) together with the carbons to which they are bound, may form a cyclopentyl, cyclohexyl or cycloheptyl endo ring, or (b) be substituted; when m is 2 then (I) represents a substituted 1,5-diazacycloheptane, and when m is 6 and cyclized then (I) typically represents a substituted decahydrobenozdiazepine;

$R_1$ and $R_5$ independently represent hydrogen, alkyl having from 1 to 24 carbon atoms, hydroxyalkyl having from 1 to 12 carbon atoms, ether having from 3 to 18 carbon atoms, hydroxyalkyl ether having from 4 to 18 carbon atoms, aralkyl having from 7 to 24 carbon atoms, and cycloalkyl having from 6 to 7 carbon atoms;

$R_2$ represents hydrogen or lower alkyl having from 1 to 5 carbon atoms;

$R_3$ and $R_4$ independently represent alkyl having from 1 to 24 carbon atoms, cycloalkyl having from 5 to 14 carbon atoms, aralkyl having from 7 to 14 carbon atoms, and cyclizable alkylene having from 5 to 6 carbon atoms which alkylene together with the carbon atom of the diaza ring to which said alkylene is bound, represents cycloalkyl having from 6 to 7 carbon atoms.

When the compositions of this invention include a stabilizer compound having a substituted alkylene group in the variable length bridge of the above-identified structural formula (I), the compound may be represented by a structural formula selected from the group consisting of

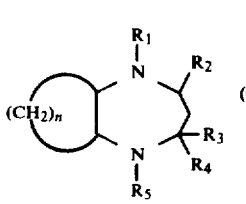 and 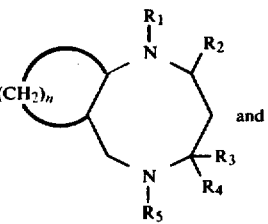

(II) (III)

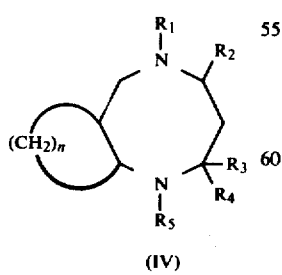

(IV)

wherein n represents an integer in the range from 4 to 6, so that when n=4, then (II) represents a tri-substituted decahydrobenzodiazepine if $R_2$ is not hydrogen.

Illustrative of the type of substituents that are effective in the above-identified bicyclo di-substituted 1,5-diazacycloalkanes are:

where $R_1$ and/or $R_5$ is alkyl, examples are methyl, ethyl, n-propyl, n-butyl, t-butyl, n-hexyl, n-octyl, 2-ethylhexyl, n-decyl, n-tetradecyl, n-octyldecyl, and the like;

where $R_1$ and/or $R_5$ is hydroxyalkyl, examples are 2-hydroxyethyl, 2-hydroxypropyl, 3-hydroxypropyl, 2-hydroxybutyl, 6-hydroxyhexyl, 8-hydroxyectyl, and the like;

where $R_1$ and/or $R_5$ is hydroxyalkylether, examples are 2-hydroxyethyloxaethyl, phenyloxapropyl, 4-hydroxybutyloxahexyl, and the like;

where $R_1$ and/or $R_5$ is aralkyl, examples are benzyl, 2-phenylethyl, 4-phenylbutyl, o,p-dimethylbenzyl, p-octylbenzyl, and the like;

where $R_1$ and/or $R_5$ is cycloalkyl, examples are cyclopentyl, methylcyclopentyl, cyclohexyl, methylcyclohexyl, cycloheptyl, dimethylcycloheptyl and cyclooctyl; and for $R_3$ and $R_4$, examples are methyl, ethyl, propyl, n-butyl, isobutyl, n-hexyl, 2-ethylheptyl, n-decyl, and where the substituents are cyclizable, cyclopentyl, methylcyclopentyl, cyclohexyl, methylcyclohexyl, piperidyl, 2-2',6-6'-tetramethylpiperidyl, and the like.

The foregoing compounds are preferably prepared by reacting an appropriately chosen diaminocycloalkane, and, an unsaturated monoketone to yield a bicyclo diazaalkene having a double bond in the diaza ring; or, with a disubstituted acid to yield the bicyclo-1,5-diazaalkan-2-one, as described hereinabove. For example, 1,2-diaminocyclohexane reacts with mesityl oxide in a solution of hexanes, and in the presence of potassium carbonate, to yield 2,4,4-trimethyl-$H^1$-2,3,5,6,7,8,9,10-octahydro-1,5-benzodiazepine which is preferably hydrogenated under pressure in the presence of catalyst, to yield decahydrobenzodiazepine.

Examples of specific disubstituted bicyclo 1,5-diazacycloalkanes where the $N^5$-adjacent C atom is disubstituted, including when the substituents are cyclized, are cis- and trans- isomers of bicyclo-1,5-diazacycloalkanes such as 2,2,4-trialkyl-decahydro-1,5-benzodiazepine; 4,4-dialkyl-decahydro-1,5-benzodiazepine; and the like.

Most preferred are the cis- and trans- isomers of 1(or 5)-alkyl (or hydroxyalkyl)-4,4-dialkyl-decahydrobenzodiazepines having the structure

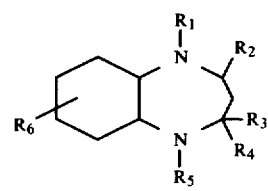

wherein $R_1$–$R_5$ have the same connotation as stated hereinabove, and $R_6$ is chosen from hydrogen and lower alkyl which may be present as a substituent on one, two or three carbons of the cyclohexyl endo ring. Where $R_6$ is hydrogen, examples of preferred stabilizers are:

cis-1-(n-butyl)decahydro-4,4-dimethyl-1,5-benzodiazepine;

cis- and trans-4,4-dimethyl-decahydro-1,5-benzodiazepine;

cis- and trans-$N^1$, $N^5$-bis[2-hydroxyethyl-4,4-dimethyl-decahydro-1,5-benzodiazepine];

cis- and trans-$N^1$, $N^5$-bis[2-hydroxyethyl-4,4-diethyl-decahydro-1,5-benzodiazepine];

cis- and trans-$N^1$, $N^5$-bis[2-hydroxyethyl-4-methyl-4-ethyl-decahydro-1,5-benzo diazepine];

cis- and trans-$N^1$, $N^5$-bis[2-hydroxyethyl-4,4-pentamethylene-decahydro-1,5-benzo-diazepine];

cis-1-(n butyl)-decahydro-2-methyl-4,4-dimethyl-1,5-benzodiazepine;

cis- and trans-4,4-pentamethylene-decahydro-1,5-benzodiazepine;

cis- and trans-$N^1$-methyl,$N^5$-methyl-4,4-dimethyl-decahydrobenzodiazepine;

cis- and trans-$N^1$-benzyl,$N^5$-benzyl-4,4-dimethyl-decahydrobenzodiazepine.

The foregoing last named alkylated bicyclo substituted 1,5-diazacycloalkanes are readily prepared by alkylating an $N^1$ or $N^5$ position on the diaza ring, after first preparing the desired substituted diazacycloalkane. Since it is not easy to selectively alkylate one position or the other, it will be found that both positions are alkylated. Any conventional means for alkylating may be employed, it being convenient to do so with methyl iodide or benzyl chloride.

The bicyclo diazacycloalkanes may be used to prepare bis compounds. These bis compounds are readily formed by reacting the diazacycloalkane having unsubstituted N atoms (that is, $R_1$ and $R_5$ are hydrogen) with a dihaloalkane, ditosylated alcohol, or other compound (for example, m- or p-xylene) with leading groups so as to react with the diazacycloalkane at the N positions and form a bridge for the bis compound. The bis compounds formed have the structure

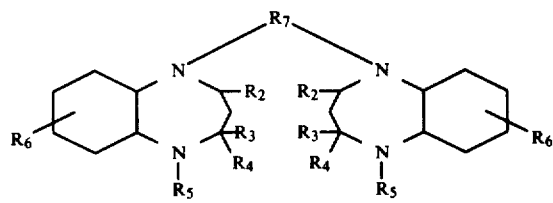

wherein $R_7$ is selected from the group consisting of phenyl and $(CH_2)_p$ where p is an integer in the range from 2 to 10.

Though the structure of only a particular bis compound is illustrated hereinabove (one connected through the $N^1$ atoms of each diazacycloalkane moiety), it will readily be recognized that, since the $N^1$ and $N^5$ positions are each relatively readily attacked, the bis(-diazacycloalkane) formed usually results in bridging through both the $N^1$ and $N^5$ positions, and the bis compounds formed will consist essentially of a mixture of bis compounds. Thus, a mixture of bis compounds will have two bicyclo diazacycloalkane moieties connected through the following N atoms of each separate moiety: $N^1$ and $N^5$; $N^1$ and $N^1$; and/or $N^5$ and $N^5$. When a mixture of bis compounds is formed, the mixture is used to stabilize a normally solid polymer against uv light degradation.

Most preferred bis compounds are the cis- and trans-isomers of 1,4-butane-bis[4,4-dimethyl-decahydro-1,5-benzodiazepine];

1,5-pentane-bis[4,4-dimethyl-decahydro-1,5-benzodiazepine];

1,6-hexane-bis[4,4-dimethyl-decahydro-1,5-benzodiazepine];

1,4-xylene-bis[4,4-dimethyl-decahydro-1,5-benzodiazepine]; and, 1,3-xylene-bis[4,4-dimethyl-decahydro-1,5-benzodiazepine].

Compositions of this invention are organic compounds which have been stabilized to combat the deleterious effect of thermal, oxidative or actinic light such as are usually evidenced by discoloration and/or embrittlement. These compounds can be low or high molecular weight materials, and particularly include homopolymers, copolymers and mixtures thereof. Examples of compounds that can be stabilized against degradation due to UV light are oils; monomers, particularly $\alpha$-$\beta$-olefinically unsaturated monomers such as acrylates, dienes, vinyl nitriles, and the like; and other lower molecular weight materials such as alcohols, aldehydes, and the like. Examples of known organic compounds or substrates which can be stablized with polysubstituted 2-keto diazacycloalkanes are natural rubber, synthetic rubbers such as cis-polyisoprene, styrene-butadiene rubber, diene-nitrile rubbers, polyepihalohydrin polymers, and the like, polyurethanes, PVC resins, ABS resins, polystyrene, polyacrylonitrile, polymethacrylates, polycarbonates, varnish, phenol-formaldehyde resins, polyepoxides, polyesters, and polyolefin homo and copolymers such as polyethylene, polypropylene, ethylene-propylene polymers, ethylene-propylenediene polymers, ethylenevinyl acetate polymers and the like. The substituted 2-ketodiazacycloalkanes can also be used to stabilize mixtures and blends of polymeric materials such as ABS resinblends, PVC and polymethacrylate blends, and blends of polyolefin homopolymers and copolymers such as blends of polypropylene in epdm polymers.

The substituted 1,5-diazacycloalkanes are particularly useful as UV stabilizers for normally solid polymers such as the poly-$\alpha$-monoolefin homopolymers of $\alpha$-olefins having up to 3 carbon atoms, e.g. ethylenepropylene and their copolymers; vinyl resins formed from the polymerization of vinyl halides or from copolymerization of vinyl helides with unsaturated polymerizable compounds, for example vinyl esters, $\alpha,\beta$-unsaturated acids, $\alpha,\beta$-unsaturated esters and unsaturated hydrocarbons; polyurethanes such as are prepared from polyols and an organic polyisocyanate; polyamides such as polymethyleneterephthalates; polycarbonates such as those prepared from bisphenol-A and phosgene; polyacetals; polyethylene oxide; polyacrylics such as polyacrylonitrile; polyphenyleneoxides such as those prepared from 2,6-dimethylphenol and the like. The $\alpha$-monoolefin monomers used to prepare the latter polymers include ethylene, propylene, isobutylene, 1-butene, 1-pentene, 1-hexene, 4-methyl-1-pentene, and the like. Excellent results have been obtained using compounds of this invention, as well as known substituted 1,5-diazacycloalkanes to stabilize polypropylene against UV degradation.

The stabilized compositions of this invention are especially useful in those instances where the plastic article made from the stabilized composition is to be used outdoors, or indoors under intense actinic light.

Many known compounding ingredients may be used along with the substituted 1,5-diazacycloalkanes in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearated, sebacates, azelates, phthalates, the like; ASTM type 2 petroleum oils, paraffinic oils, castor oil, tall oil, glycerin, and the like; antioxidants such as 2,6-di-t-butyl paracresol; 2,2'-methylenebis-(4-ethyl-6-t-butylphenol); 2,2'-thiobis-4-methyl-6-t-butyl-phenol); 2,2'-methylenebis-6-t-butyl-4-ethyl-phenol; 4,4'-butylenebis-(6-t-butyl-m-cresol); 2-(4-hydroxy-3,5-di-t-butylanilino)-4,6-bis(octylthio)-1,3,5-triazine; hexahydro-1,3,5-tris- -(3,5-di-t-butyl-4-hydroxyphenyl)propionyl-s-triazine; tris-(3,5-di-t-butyl-4-hydroxybenzyl)isocyanurate; tetrakismethylene-3(3',5'-di-t-butyl-4'-hydroxyphenyl) propionate methane; distearyl thiodipropionate; dilauryl thiodipropionate; tri(-nonylphenyl)phosphite; tin thioglycolate; and the like; and the other ingredients such as pigments, tackifiers, flame retardants, fungicides, and the like.

Compounding ingredients of particular interest to be used in the compositions of the invention are the antioxidant stabilizers. As the 1,5-diazacycloalkane compounds of the invention are UV stabilizers, it is beneficial to add antioxidants to the compositions of the invention to achieve both UV light and oxygen stability of the compositions. The antioxidants are used in the range from about 0.1 part to about 20 parts by weight, preferably from about 0.2 part to about 5 parts by weight per 100 parts by weight of the material. Of the types of antioxidants to be used, are phosphate, sulfide and phenolic antioxidants, the last being preferred.

Examples of phenolic antioxidants are 2,6-di-t-butyl-phenol; 2-methyl-4,6-dinonyl phenol; 2,6-di-t-butyl-p-cresol; 2,2'-methylene-bis-(4-methyl-6-t-butyl phenol); 1,1'-methylene-bis-(2-naphthol); 4,4'-methylene-bis-(2,6-di-t-butyl phenol); 4,4'-tio-bis (6-t-butyl-m-cresol); and the like. Although any phenolic antioxidant used in combination with the substituted 2-keto diazacycloalkanes would improve the heat and oxygen stability of the compositions, the more preferred phenolic antioxidants are those having alkylhydroxyphenyl substituents on an ester or a heterocyclic nucleus.

Examples of phenolic antioxidants having alkylhydroxyphenyl substituents on an ester nucleus are compounds disclosed in U.S. Pat. No. 3,330,859 exemplified by di-lauryl α,α-bis(3,5-di-t-butyl-4-hydroxybenzyl)malonate; and disclosed in U.S. Pat. No. 3,627,725 exemplified by tetrakis (methylene-3-(3',5'-di-t-butyl-4'-hydroxyphenyl)propionate) methane; and the like.

Examples of phenolic antioxidant compounds having alkylhydroxyphenyl substituents on a heterocyclic nucleus are compounds where the heterocyclic nucleus is a triazine nucleus such as compounds disclosed in British Pat. No. 977,589 and exemplified by 2,4,6-tris(4-hydroxy-3,5-di-t-butyl benxylthio)-1,3,5-triazine; compounds disclosed in U.S. Pat. No. 3,706,740 and exemplified by 2,3,6-tris(3',5'-di-t-butyl-4'-hydroxybenzyl)-1,3,5-triazine; disclosed in U.S. Pat. No. 3,567,724 and exemplified by hexahydro-1,3,5-tris-3-(3,5-di-t-butyl-4-hydroxyphenyl) propionyl-s-triazine; disclosed in U.S. Pat. No. 3,694,440 and exemplified by 1,3,5-tris(4'-hydroxy-3',5'-di-t-butylphenylpropionyloxyethylthiopropionyl)hexahydro-1,3,5-triazine; and the like.

Examples of phenolic antioxidant compounds having alkylhydroxyphenyl substituents on a isocyanurate nucleus are compounds of the formula disclosed in U.S. Pat. No. 3,531,483 and exemplified by tris-(3,5-di-t-butyl-4-hydroxybenzyl) isocyanurate; disclosed in U.S. Pat. No. 3,678,047 and exemplified by 2,2'2''-tris(3-(3,5-di-t-butyl-4-hydroxyphenyl)propionyloxy)ethyl isocyanourate; and the like.

Still other hindered phenols useful as thermal antioxidants are disclosed in U.S. Pat. No. 3,920,659, and in copending U.S. patent application Ser. Nos. 697,345 and 697,387 which are incorporated herein by reference as if fully set forth.

The substituted 1,5-diazacycloalkane stabilizers, and the other compounding ingredients if used, can be admixed with substrates using known mixing techniques and equipment such as internal mixing kettles, a Banbury mixer, a Henschel mixer, a two-roll mill, an extruder mixer, or other standard equipment, to yield a composition which may be extruded, pressed, blow-molded or the like into film, fiber or shaped articles. Standard mixing times and temperatures can be employed. The objective is to obtain intimate and uniform mixing of the components. A favorable mixing procedure to use when adding the diazacycloalkane compound to a plastic material is to either dissolve or suspend the compound in a liquid such as hexane or benzene, add the plastic material in the form of a powder to the solution or suspension, evaporate off the liquid, and extruder mix the stabilized plastic material prior to forming the product.

The UV stability of a particular composition containing a polymeric material and a substituted diazacycloalkane can be evaluated by exposing a prepared sample of the composition to Xenon or Carbon Arc light in a Weather-O-meter operating at a temperature, for example, of about 140° F. (60° C.). Degradation of the sample can be followed by periodically measuring the hydroperoxide absorption band at 3460 cm$^{-1}$ or carbonyl absorption band at 1720 cm$^{-1}$ using an IR Spectrophotometer. The rapid formation of carbonyl indicates failure of the sample. This test procedure is well known, and is published in the text *Photodegradation, Photo-oxidation and Photostabilization of Polymers* by Ranby and Rabek, John Wiley & Sons, N.Y., N.Y., (1975) at page 129 et seq., and is disclosed in U.S. Pat. No. 3,909,493. Failure of the sample is also checked by visual signs of cracking when the sample is bent 180°.

Samples of the compositions can also be checked for oxidative and thermal stability by measuring the time to discoloration and/or embrittlement of the sample after aging in an air circulating over at 140° C.

EXAMPLES

The following examples are given to further illustrate the invention. Detailed procedures are set forth for the preparation of compounds and compositions of this invention.

EXAMPLE 1

Preparation of 2,4,4-trimethyl-1,5-decahydrobenzodiazepine

To a solution of 30 ml hexanes and 9.8 g mesityl oxide, 13.8 g potassium carbonate and 11.4 g 1,2-diaminocyclohexane were added. The mixture was stirred overnight under argon and refluxed for 70 hrs. Upon cooling the mixture was filtered, and the solvent removed. After distillation at 79°-83° C. under 9 mm hg, 10.5 g colorless oil is collected. The oil was dissolved in 100 ml ethanol and hydrogenated with 1 g Raney-Nickel at 100° C. and 1000 psi overnight. Upon cooling it was filtered and concentrated to yield a colorless oil. The oil was distilled and the fraction at 112°-8° C. under 9 mm Hg vacuum was collected.

The structure of the compound is supported by IR, NMR, and mass spectrometer data.

EXAMPLE 2

Preparation of N$^1$,N$^5$-bis-β-hydroxyethyl-2,4,4-trimethyl-1,5-decahydrobenzodiazepine 10 g of 2,4,4-trimethyl-1,5-decahydrobenzodiazepin, prepared as described in Example 1 hereinabove, and 8.8 g ethylene oxide were mixed with 2 ml ethanol as catalyst and heated to 180° C. in an autoclave for 8.5 hrs. Cooled down and distilled the oil to collect yellow oil at 210°-220° C. and 10.25 mm.

The following Table I sets forth data obtained on tests conducted with 20 ml thickness samples of polypropylene. All samples contain 0.5 parts stabilizer per 100 parts resin (phr) and also include 0.25 phr of Irganox 1010 antioxidant.

TABLE I

| Ex* | | Xenon Weather-ometer Hours | Oven Aging (140° C.) Hours |
|---|---|---|---|
| | NONE | 400 | n.a. |
| | Tinuvin ® 327: 2-(3',5'-di-t-butyl-2'-hydroxyphenyl-5-chlorobenzotriazole | 1250 | 2616 |
| | +Cyasorb ™ 531 | 6000 | 2700 |
| 1 | 2,4,4-trimethyl-1,5-decahydro-benzodiazepine | 710 | 2300 |
| 2 | mixture of cis- and trans-4,4-dimethyl-decahydro 1,5-benzodiazepine | 1830 | 2520 |
| 3 | mixture of cis- and trans-N$^1$,N$^5$—bis[-hydroxyethyl 4,4-dimethyl-decahydro-1,5-benzodiazepine] | 1650 | 2430 |
| 4 | 1,4-butane-bis[4,4-dimethyl-decahydro-1,5-benzodiazepine] | 1980 | 2640 |

*The sample tested in each example contains the specified stabilizer prepared in a manner analogous to that described in the specification hereinabove.
+ available from American Cyanamid Co.

We claim:

1. A composition of matter resistant to degradation by ultraviolet light comprising an ultraviolet light degradable normally solid polymer having dispersed therein from about 0.01 part to 5 parts by weight of a polysubstituted bicyclic 1,5-diazacycloalkane stabilizer, per 100 parts of said solid polymer, said stabilizer being represented by a moiety having a structure selected from the group consisting of

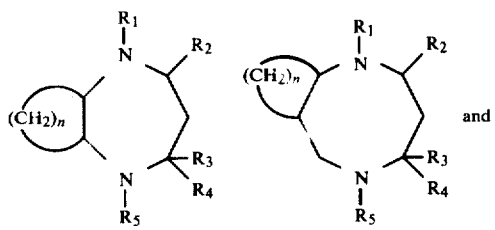

and

-continued

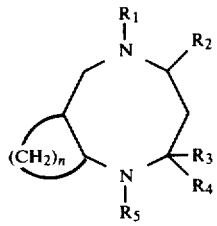

wherein,
n is an integer in the range from 4 to 6;
R$_1$ and R$_5$ independently represent hydrogen, alkyl having from 1 to 24 carbon atoms, hydroxyalkyl having from 1 to 12 carbon atoms, ether having from 3 to 18 carbon atoms, hydroxyalkyl ether having from 4 to 18 carbon atoms, aralkyl having from 7 to 24 carbon atoms, and cycloalkyl having from 6 to 7 carbon atoms;
R$_2$ represents hydrogen or lower alkyl having from 1 to 5 carbon atoms; and
R$_3$ and R$_4$ independently represent alkyl having from 1 to 24 carbon atoms, cycloalkyl having from 5 to 14 carbon atoms, aralkyl having from 7 to 14 carbon atoms, and cyclizable alkylene having from 5 to 6 carbon atoms which alkylene together with the carbon atom of the diaza ring to which said alkylene is bound, represents cycloalkyl having from 6 to 7 carbon atoms.

2. The composition of claim 1 wherein R$_1$ or R$_5$ is selected from the group consisting of alkyl having from 1 to 20 carbon atoms, and hydroxyalkyl having from 2 to 8 carbon atoms; and
R$_2$, R$_3$, and R$_4$ are each lower alkyl having from 1 to 5 carbon atoms.

3. The composition of claim 1 wherein n=4.

4. The composition of claim 3 wherein said stabilizer is selected from the group consisting of
cis-4,4-dimethyl-decahydro-1,5-benzodiazepine;
trans-4,4-dimethyl-decahydro-1,5-benzodiazepine;
cis-N$^1$, N$^5$-bis[2-hydroxyethyl-4,4-dimethyl-decahydro-1,5-benzodiazepine];
trans-N$^1$, N$^5$-bis[-hydroxyethyl-4,4-dimethyl-decahydro-1,5-benzodiazepine].

5. A composition of matter resistant to degradation by ultraviolet light comprising an ultraviolet light degradable normally solid polymer having dispersed therein from about 0.01 part to 5 parts by weight of a bis compound of a polysubstituted bicyclic 1,5-diazacycloalkane stabilizer, per 100 parts of said solid polymer, said stabilizer being represented by two connected moieties each having a structure

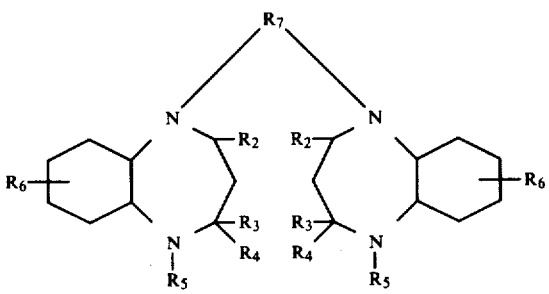

wherein, said bis compound consists essentially of said two moieties connected through one of the N atoms of each moiety, and the other N atom of each moiety is attached to a member selected from the group consisting of hydrogen, alkyl having from 1 to 24 carbon atoms, hydroxyalkyl having from 1 to 12 carbon atoms, ether having from 3 to 18 carbon atoms, hydroxyalkyl ether having from 4 to 18 carbon toms, aralkyl having from 7 to 24 carbon atoms, and cycloalkyl having from 6 to 7 carbon atoms;

$R_2$ and $R_6$ independently represent hydrogen or lower alkyl having from 1 to 5 carbon atoms;

$R_3$ and $R_4$ independently represent alkyl having from 1 to 24 carbon atoms, cycloalkyl having from 5 to 14 carbon atoms, aralkyl having from 7 to 14 carbon atoms, and cyclizable alkylene having from 5 to 6 carbon atoms which alkylene together with the carbon atom of the diaza ring to which said alkylene is bound, represents cycloalkyl having from 6 to 7 carbon atoms; and, $R_7$ is selected from phenyl and $(CH_2)_p$ where p is an integer in the range from 2 to 10.

6. The composition of claim 5 wherein the connecting group is polymethylene having from 2 to 10 carbon atoms.

7. The composition of claim 5 wherein said stabilizer consists essentially of a mixture of bis compounds including at least two said moieties connected through the following N atoms of each separate moiety: $N^1$ and $N^1$; $N^1$ and $N^5$; and, $N^5$ and $N^5$.

8. The composition of claim 7 wherein said bis compound is selected from the group consisting of
1,4-butane-bis[4,4-dimethyl-decahydro-1,5-benzodiazepine];
1,5-pentane-bis[4,4-dimethyl-decahydro-1,5-benzodiazepine];
1,6-hexane-bis[4,4-dimethyl-decahydro-1,5-benzodiazepine];
1,4-xylene-bis[4,4-dimethyl-decahydro-1,5-benzodiazepine]; and,
1,3-xylene-bis[4,4-dimethyl-decahydro-1,5-benzodiazepine].

* * * * *